United States Patent [19]

Marinak et al.

[11] Patent Number: 4,564,681

[45] Date of Patent: * Jan. 14, 1986

[54] PRODUCTION OF MIXTURES RICH IN 3-CHLORO-2-TRICHLOROMETHYL PYRIDINE

[75] Inventors: Michael J. Marinak, Kelso; John L. Simonson, Longview, both of Wash.

[73] Assignee: Kalama Chemical, Inc., Kalama, Wash.

[*] Notice: The portion of the term of this patent subsequent to Dec. 11, 2001 has been disclaimed.

[21] Appl. No.: 422,751

[22] Filed: Sep. 24, 1982

[51] Int. Cl.$^4$ .......................................... C07D 213/61
[52] U.S. Cl. ..................................... 546/345; 546/346
[58] Field of Search ................................ 546/345, 346

[56] References Cited

U.S. PATENT DOCUMENTS

| | | | |
|---|---|---|---|
| 2,516,402 | 7/1950 | McBee | 546/345 |
| 2,679,453 | 5/1954 | Brett et al. | 71/94 |
| 3,186,994 | 3/1965 | Johnston et al. | 546/345 |
| 3,256,167 | 4/1966 | Norton et al. | 546/345 |
| 3,317,549 | 5/1967 | Johnston | 546/286 |
| 3,418,323 | 8/1968 | Johnston et al. | 546/345 |
| 3,424,754 | 2/1969 | Taplin, III | 546/345 |
| 4,487,935 | 12/1984 | Marinak et al. | 546/345 |
| 4,515,953 | 5/1985 | Marinak et al. | 546/345 |

FOREIGN PATENT DOCUMENTS 957276  6/1964  United Kingdom ................ 546/345

OTHER PUBLICATIONS

Pesticide Manufacturing and Toxic Materials Control Encyclopedia (1980), pp. 289–290.
William James Sell (J. Chem. Soc., vol. 87, pp. 799 et seq (1905).
Kosorotov et al, Zhurnal Organischeskoi Khimii, vol. 16, No. 10, pp. 2163–2171, Oct. 1980 (English Translation).

*Primary Examiner*—Joseph Paul Brust
*Attorney, Agent, or Firm*—Graybeal & Cullom

[57] ABSTRACT

Preparation of high yields of mixtures rich in 3-chloro-2-trichloromethyl pyridine by maintaining a chlorine to alpha-picoline weight ratio of at least about 8:1 when feeding alpha-picoline hydrochloride and excess chlorine to reactor means at a temperature in the range of about 135° C. to about 170° C. and in the absence of a catalyst, the reactants being contained in a well mixed diluent producing essentially no hydrogen chloride by reaction with chlorine in the indicated temperature range.

4 Claims, 1 Drawing Figure

4,564,681

PRODUCTION OF MIXTURES RICH IN 3-CHLORO-2-TRICHLOROMETHYL PYRIDINE

BACKGROUND OF THE INVENTION

1. Field of the Invention

The present invention relates to preparation of mixtures rich in 3-chloro-2-trichloromethyl pyridine by non-catalytic liquid phase chlorination of alpha-picoline hydrochloride. 3-chloro-2-trichloromethyl pyridine is useful, for example, as an intermediate in the preparation of various herbicidal compositions as described in Johnston et al U.S. Pat. No. 3,317,549.

2. Description of the Prior Art

Known processes for preparation of 3-chloro-2-trichloromethyl pyridine are described in Brett et al U.S. Pat. No. 2,679,453 and Johnson et al U.S. Pat. No. 3,317,549 (at page 12, lines 29–36). In the process disclosed in U.S. Pat. No. 2,679,453, alpha-picoline is chlorinated on a batch basis at a temperature from 50° C. to 150° C. in the presence of water to yield various chlorinated pyridine/picoline compositions. Taplin U.S. Pat. No. 3,424,754 describes the chlorination of alpha-picoline hydrochloride in the temperature range of from 140° C. to 230° C. to yield 6-chloro-2-trichloromethyl pyridine and compositions enriched in said compound, without any indication as to formation of any 3-chloro-2-trichloromethyl pyridine by the process. William James Sell in an article appearing at J. Chem. Soc. Vol. 87, pp 799 et seq. (1905) discloses a process of preparing alpha-picoline hydrochloride by direct addition of anhydrous hydrogen chloride gas to alpha-picoline, and the chlorination of alpha-picoline hydrochloride at temperatures of about 105° C.–110° C.

SUMMARY OF THE INVENTION

The present invention is an improvement over previously known processes for producing mixtures rich in 3-chloro-2-trichloromethyl pyridine and involves chlorinating preformed alpha-picoline hydrochloride at a temperature of from about 135° C. to about 170° C. in the presence of an essentially nonreactive diluent and in the absence of a catalyst, the chlorine and picoline hydrochloride being fed to the reaction at a chlorine-to-picoline feed ratio of at least about 8:1 by weight and the feed rate of picoline hydrochloride being low enough so that no substantial separation of the reactor charge into an unchlorinated picoline-hydrochloride lighter phase occurs. By thus appropriately controlling the reaction, yields of 3-chloro-2-trichloromethyl pyridine in excess of 20% by weight are realized.

The composition of the diluent or reaction media is important in this process, to secure good yields of the desired volatile chlorinated alpha-picoline. Its function in this invention is quite different from the initiator charge described in U.S. Pat. No. 3,424,754. In U.S. Pat. No. 3,424,754 the initiator charge has a function of evolving HCl when contacted with chlorine at the reaction temperature. In the present invention the diluent's function is to be noncompetitive for the chlorine fed to the reactor and to help remove the heat of reaction from the chlorination of the alpha-picoline hydrochloride.

Examples of some compounds which generate little if any HCl when contacted with chlorine under the reaction conditions are: 5-chloro, 6-chloro, 3,5-dichloro, 5,6-dichloro, 3,6-dichloro or 3,5,6-trichloro-2-trichloromethyl pyridine and 2,3,6-trichloro, 2,3,5,6-tetrachloro or 2,3,4,5,6-pentachloro pyridine and mixtures thereof. This list is not meant to be a complete list of all possible diluent components but is illustrative of the type that are acceptable. The diluent may be the chlorinated pyridine/picoline products of a previous reaction which meet the above criteria and is high in volatile content.

In practice of this invention, an excess of chlorine is fed relative to that theoretically needed for the alpha-picoline hydrochloride chlorinatipn which provides additional agitation and hence better mixing; as well as higher chlorine partial pressure which increases the chlorine solubility in the reaction media. Ratios in excess of 8:1 are preferred, which result in chlorine being the majority of the pressure component in the gas phase. If the initiator charge were as described in U.S. Pat. No. 3,424,754, it would compete for the available chlorine and result in much lower chlorine concentrations in the gas phase and hence lower chlorine concentrations in the reaction media when compared with a non-reactive diluent. At higher temperatures, the weight ratio of chlorine to alpha-picoline fed needs to be higher in order to achieve the high yields of the desired volatile chloro-picolines. This is necessary because the chlorine is reacting more rapidly with the alpha-picoline hydrochloride as the temperature increases and therefore this dissolved chlorine must be more rapidly replaced in the reaction medium. This is accomplished by increasing the rate of chlorine addition relative to the alpha-picoline flow rate which increases the chlorine partial pressure and hence its mole fraction in the liquid reaction medium.

Gas solubilities tend to decrease with temperature, but an increase in reactor system back pressure serves to increase the chlorine solubility. The alpha-picoline hydrochloride feed must be controlled relative to the reaction volume so no more than about 10% by volume of light liquid phase accumulates relative to the chlorinated picoline phase. Potential decomposition products can result at this temperature in the absence of cooling and excess chlorine. Alpha-picoline hydrochloride is unstable at reaction temperatures in excess of 135° C. Good mixing is necessary in order to achieve dispersion of chlorine and alpha-picoline hydrochloride into the diluent. Since alpha-picoline hydrochloride and the diluent are somewhat immiscible and of different densities, agitation to ensure good contact is required.

Care must be taken to ensure metallic impurities such as iron, copper, aluminum and other Lewis Acid type metals are excluded from the reaction medium, as they will cause different reactions in the chlorination that may not be desirable.

DESCRIPTION OF THE PREFERRED EMBODIMENTS

EXAMPLE 1

Figure 1:
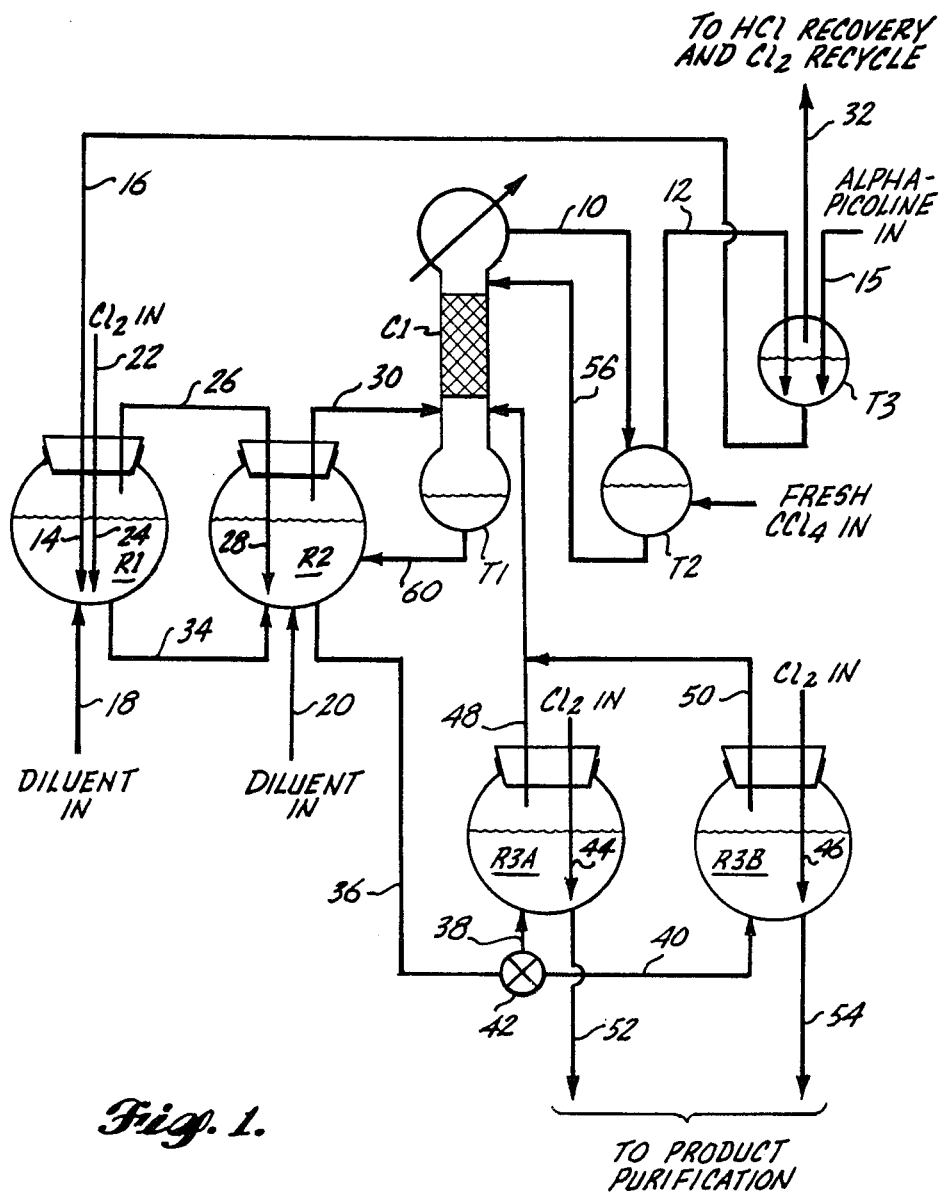
FIG. 1 is a schematic diagram of a reaction system for practicing the process of the present invention on a continuous batch basis.

FIG. 1 schematically illustrates a reaction system of a continuous batch process for producing mixtures rich in 3-chloro-2-trichloromethyl pyridine according to the present invention. Reactors R1, R2, R3A and R3B are glass of spherical configuration, electrically heated and each about 1 liter in volume. Water cooled quench column C1 is suitably of cylindrical design, 1½ inches in diameter, and containing as packing some 18 inches of ¼ inch glass rings.

Quench column C1 includes a holding tank or reservoir T1 and the overhead vapor from column C1 is delivered through vent line 10 to disengaging tank T2 in which the carbon tetrachloride collects, with the chlorine and hydrogen chloride evolving from column C1 being delivered by vent line 12 and sparged into hydrochlorination tank T3. For start up, alpha-picoline hydrochloride, previously prepared in a known manner as described by Sell, for example, is charged to hydrochlorination tank T3 and alpha-picoline hydrochloride is withdrawn from tank T3 and delivered to bottom discharging sparger 14 in reactor R1 through line 16. For start up, also, reactor R1 was charged with 850 grams of diluent, consisting of chlorinated alpha-picoline from a previous reaction (comprising 93% 6-chloro-2-trichloromethyl pyridine, 4% 3,5-dichloro-2-trichloromethyl pyridines, and 1½% 3,6-dichloro-2-trichloromethyl pyridine, by weight), as indicated at charge line 18. 300 grams of like diluent material is also charged to reactor R2 through charge line 20. The start up sequence is that of introducing the diluent to the reactor, then initiating chlorine flow, then heating the reactor to desired reaction temperature, then initiating the alpha-picoline hydrochloride flow. By this procedure the alpha-picoline hydrochloride only sees excess chlorine in the reactor and degradation thereof to non-volatiles is avoided. Once reactors R1 and R2 are charged, external heat is applied and the temperature thereof maintained at 155° C. Chlorine gas from a suitable source is delivered to the reactor R1 through feed line 24 and bottom discharging sparger 24 at a flow rate of 440 grams per hour. The flow rate of alpha-picoline hydrochloride sparged into reactor R1 through bottom discharging sparger 14, the discharge stream of which is closely adjacent to the discharge stream of chlorine sparger 24, was maintained at 44 grams alpha-picoline per hour, amounting to a chlorine to picoline feed ratio of 10:1.

As will be understood, the alpha-picoline hydrochloride fed to reactor R1 releases hydrogen chloride from both the reaction with the chlorine and the decomposition of the hydrochloride salt. This hydrogen chloride along with excess chlorine is vented from reactor R1 through vent line 26 and sparged into the charge in reactor R2 through bottom placed sparger 28, the overhead vapor including hydrogen chloride and excess chlorine being vented from reactor R2 and delivered through line 30 to quench column C1, thence through line 10 and line 12 to hydrochlorinating tank T3, the vapor flow from which passes through line 32 to hydrogen chloride and chlorine gas recovery means known per se, for recyling of the chlorine gas to the process and recovery of the hydrogen chloride as desired. Once hydrogen chloride gas is being generated and passing through the system to hydrochlorinating tank T3, the alpha-picoline feed into tank T3 through line 15 can be started.

Reactor R2 is only partially charged with diluent at start up. This is for the reason that, as the volume of the reaction mass in reactor R1 increases in the course of the reaction, a portion of the reaction mass is moved from reactor R1 to reactor R2 through discharge line 34 for further chlorination in reactor R2. Then, when the volume in reactor R2 increases to the point where the reactor R2 is filled to its operating level, further increase in its volume is taken care of by progressively discharging the excess through line 36 to either reactor R3A through line 38, or to reactor R3B through line 40, depending on the setting of valve 42. Chlorination to process end point is completed in either reactor R3A or reactor R3B by continuing introduction of chlorine gas through bottom discharging spargers 44, 46, with continued heating of the reactors R3A and R3B to a the same temperature, i.e. at a temperature of 155° C. in the selected example. Chlorine and hydrogen chloride vapor take off from reactors R3A and.R3B is delivered through vent lines 48, 50 to quench column C1. Chlorinated reaction product is withdrawn from the reactors R3A and R3B through respective discharge lines 52, 54, with the product going to product purification means known per se, such as a vacuum fractional distillation column. Liquid discharge from holding tank T2 is delivered to column C1 through line 56 to return carbon tetrachloride to the column C1, with make up of carbon tetrachloride from an appropriate supply if necessary, as indicated at 58. The liquid phase fraction collecting in bottom tank T1 of the quench column C1 is returned to reactor R2, as indicated at line 60.

Reactors R3A and R3B may be smaller or larger than reactors R1 and R2, depending on the desired residence time to complete the chlorination reaction. For example, with a reaction temperature of 155° C. and a residence time of 4½ hours in each of the reactors R1 and R2, the time required to complete the reaction in reactor R3A or in reactor R3B is about 5 hours at the same temperature. Chlorination time in the reactor R3A of the reactor R3B is controlled to minimize the concentration of 6-chloro-2-dichloromethyl pyridine and 3,4,5-trichloro-2-dichloromethyl pyridine and to maximize the concentration of 3-chloro-2-trichloromethyl pyridine. The dichloromethyl compounds are less thermally stable than the trichloromethyl pyridine compound and tend to degrade during the vacuum distillation, causing corrosion and plugging problems. Optimally, a balance is maintained which involves some toleration of dichloromethyl compound degradation to arrive at a maximal 3-chloro-2-trichloromethyl pyridine recovery.

Excess chlorine, hydrogen chloride, and some volatile corrosive chloro-picoline hydrochloride and entrained products are transferred to reactor R2 from reactor R1 by heated vent line 26 and bottom discharging sparger 28, with the volatile hydrochlorides being absorbed and reacted further in reactor R2. These hydrochlorides are very corrosive and tend to form solids on condenser surfaces that are in the 30° C. to 100° C. temperature range, the operating temperature range of quench column C1, and would therefore cause a plugging problem if passed directly from reactor R1 to the column C1. Their absorption and further reaction in reactor R2 eliminate any such plugging problem since they are essentially undetectable in the vent line 30 from reactor R2. The excess chlorine, hydrogen chloride, and entrained products passing to column C1 through reactor R2 to vent line 30 are there scrubbed with carbon tetrachloride discharged at column C1 through line 56. The entrained products build-up in hold tank T1 and the liquid level therein is controlled by recycling the excess liquid back to reactor R2 through discharge line 60.

As will be apparent, the operation of reactors R3A and R3B is in a batch manner, permitting one to be on line while the other is having the chlorinated product removed or is being filled from reactor R2. Analysis of the reaction mass in the on line reactor R3A or R3B for residual dichloromethyl compounds indicates when the reaction is finished. When this occurs, the contents of the on line reactor R3A or R3B are pumped to the purification section of the system through respective discharge line 52 or 54.

The residence time in each reactor R1, R2 and R3A or R3B varies from about 5 hours to about 10 hours, and the total cycle time in the reactors is about 15 to 30 hours. From the previously described feed and reaction conditions in Example 1, 108 grams per hour of product that contained about 21% 3-chloro-2-trichloromethyl pyridine was produced, the other major reaction product compounds being about 20% 2-trichloromethyl pyridine and about 23% 3,5-dichloro-2-trichloromethyl pyridine. As known, these dichloro compounds can be separated and processed further, such as described in U.S. Pat. Nos. 3,418,323 and 4,256,894.

In the example selected the total residence time was about 15 hours. Variation in residence time is determinable on a predictable basis, taking into consideration the product composition desired, the reactor pressure and the reactor temperature. Total residence times of less than 5 hours are possible. In any event, the feed rate of alpha-picoline hydrochloride relative to the reaction volume is to be controlled so that no greater than about 10% by volume of lighter phase (undiluted picoline hydrochloride) exists in the reaction mass.

The gases in vent line 32 from hydrochlorination tank T3 are predominantly excess chlorine and hydrogen chloride, which stream can be separated or purified by a number of conventional techniques such as absorption of the hydrogen chloride water, or drying the chlorine and compressing the chlorine gas for recycle, or by fractional distillation.

EXAMPLES 2 THROUGH 8

Examples 2 through 8 serve to illustrate some of the process variables which can occur with respect to the process of the present invention, and for such purpose were conducted on a simplified, batch process basis. A chlorination reactor comprising a 250 ml spherical glass reactor, heated by an electric heating mantle, was equipped with two sparge tubes and a vent line to a caustic scrubber. The spargers were bottom placed and closely spaced (2 cm apart) and the respective feed lines to the spargers were fed through rotometers and flow controlled through respective needle valves, one being supplied from a source of chlorine gas and the other supplied from a source of preformed alpha-picoline hydrochloride. In each run the procedure followed was the same except for the variables investigated, namely temperature, chlorine-to-picoline feed ratio, residence time, and picoline hydrochloride flow rate relative to reaction mass volume. In Example 2, which is illustrative, the reactor was charged with 50 grams of the essentially nonreactive chloro-picoline/pyridine diluent, and chlorine feed was initiated through the chlorine sparger at a rate of 70 grams per hour and the charge heated to a temperature of 155° C. Alpha-picoline hydrochloride feed was then commenced at the rate of 7 grams alpha-picoline per hour through its sparger, with both feeds continuing for a period of 6 hours. In Example 2 the chlorine to alpha-picoline feed ratio by weight during this period was 10:1. The alpha-picoline hydrochloride feed was then stopped, the temperature maintained at 155° C. and the chlorine feed was continued for an additional 2 hours at a feed rate of 70 grams per hour. The gross weight of the resulting reaction product was 155 grams, indicating a net product production of 105 grams. The processing parameters were as set forth in the following Table ONE and the constituency of the reaction product produced was as set forth in the following Table TWO. As reflected by these Tables, the product constituency in the instance of Example 2 was 20.8% 3-chloro-2-trichloromethyl pyridine, 23.9% 2-trichloromethyl pyridine, 16.5% 6-chloro-2-trichloromethyl pyridine and 10.0% 5-chloro-2-trichloromethyl pyridine, by weight, determined by gas chromatography. In the instance of Example 2, also, the volatiles present were greater than 99% by weight, as measured by internal standard gas chromatography, and the overall yield of 3-chloro-2-trichloromethyl pyridine was about 20% by weight. As indicated, additional runs, designated Examples 3, 4, 5, 6, 7 and 8, involved the processing parameters set forth in Table ONE and produced reaction products comprising the compounds set forth in Table TWO. Example 7 demonstrates that a reaction temperature of 185° C. is excessive in that such a reaction does not produce an adequate amount of the desired product. Example 8 demonstrates, on the other hand, that a reaction temperature of 125° C. is insufficient for the purpose.

TABLE ONE

|  | Ex 2 | Ex 3 | Ex 4 | Ex 5 | Ex 6 | Ex 7 | Ex 8 |
|---|---|---|---|---|---|---|---|
| Initial Reactor Temp | 155° C. | 170° C. | 170° C. | 145° C. | 135° C. | 185° C. | 125° C. |
| Diluent charge | 50 gms | 50 gms | 50 gms | 50 gms | 50 gms | 50 gms | 50 gms |
| Initial Reaction Temp | 155° C. | 170° C. | 170° C. | 145° C. | 135° C. | 185° C. | 125° C. |
| $Cl_2$ Flow Rate | 70 gms/hr | 65 gms/hr | 110 gms/hr | 70 gms/hr | 70 gms/hr | 70 gms/hr | 50 gms/hr |
| Alpha-Picoline hydrochloride flow rate (as -picoline) | 7 gms/hr | 5 gms/hr | 4.5 gms/hr | 3.3 gms/hr | 6.5 gms/hr | 4.75 gms/hr | 3.3 gms/hr |
| $Cl_2$ alpha-picoline ratio (by weight) | 10:1 | 13:1 | 25:1 | 22:1 | 11:1 | 15:1 | 15:1 |
| Reaction Time | 6 hrs | 6 hrs | 5 hrs | 5 hrs | 5 hrs | 6 hrs | 5 hrs |

TABLE ONE-continued

|  | Ex 2 | Ex 3 | Ex 4 | Ex 5 | Ex 6 | Ex 7 | Ex 8 |
|---|---|---|---|---|---|---|---|
| with both Cl$_2$ and -picoline feeds | | | | | | | |
| Additional reaction time and temp with Cl$_2$ feed only | 2 hrs @ 155° C. | 2 hrs @ 170° C. | 2 hrs @ 170° C. | 2 hrs @ 145° C. | 2 hrs @ 135° C. | 10 hrs @ 200° C. | 2 hrs @ 125° C. |
| Amt of product produced | 105 gms | 79 gms | 55 gms | 39 gms | 71 gms | 70 gms | 40 gms |
| Volatility of produced product | >99% | >99% | >99% | 98% | 96% | 97% | >97% |
| Yield of 3-chloro-2-trichloromethyl pyridine (by weight) | 20% | 14% | 14% | 18% | 14.6% | <1% | 9.5% |

In Example 2, the composition of the diluent used as the initial charge to the reactor was 12% 5-chloro-2-trichloromethyl pyridine, 10% 6-chloro-2-trichloromethyl pyridine, 26% 3,5-dichloro-2-trichloromethyl pyridine, 10% 3,6-dichloro-2-trichloromethyl pyridine, 11% 5,6-dichloro-2-trichloromethyl pyridine, 8% 3,4,5-trichloro-2-trichloromethyl pyridine, 10% 3,5,6-trichloro-2-trichloromethyl pyridine and 10% 2,3,5,6-tetrachloro pyridine, by weight.

In Examples 3 and 7 the diluent initial charge had a composition of 90% 6-chloro-2-trichloromethyl pyridine, 2% 3,6-dichloro-2-trichloromethyl pyridine, 6% 5,6-dichloro-2-trichloromethyl pyridine, and 1% pentachloro pyridine, by weight.

In Example 4, the composition of the diluent initial charge was 96% 6-chloro-2-trichloromethyl pyridine and 3% pentachloro pyridine, by weight.

In Examples 5, 6 and 8, the composition of the diluent initial charge was 85% 6-chloro-2-trichloromethyl pyridine, 6% 3,5-dichloro-2-trichloromethyl pyridine, 3% 3,6-dichloro-2-trichloromethyl pyridine, and 3% 5-chloro-2-trichloromethyl pyridine, by weight.

TABLE TWO

| | Ex 2 155° C. Temp | Ex 3 170° C. Temp Cl$_2$/Pic/13/1 | Ex 4 170° C. Temp Cl$_2$/Pic/25/1 | Ex 5 145° C. Temp | Ex 6 135° C. Temp | Ex 7 185° C. Temp | Ex 8 125° C. Temp |
|---|---|---|---|---|---|---|---|
| 2-CCl$_3$ pyridine | 23.9% | 53.7% | 49.0% | 25.5% | 9.1% | 40.0% | — |
| 6-Cl-2-CHCl$_2$ pyridine | 2.0% | — | — | 6.4% | 3.7% | — | 2.9% |
| 6-Cl-2-CCl$_3$ pyridine | 16.5% | 2.0% | — | — | 7.0% | 29.0% | — |
| 3-Cl-2-CCl$_3$ pyridine | 20.8% | 14.1% | 14.0% | 18.2% | 14.6% | — | 9.5% |
| 3,6-diCl-2-CCl$_3$ pyridine | 1.2% | 1.3% | 1.7% | 2.0% | 1.2% | 3.2% | — |

TABLE TWO-continued

| Structure | Ex 2 155° C. Temp | Ex 3 170° C. Temp Cl₂/Pic/13/1 | Ex 4 170° C. Temp Cl₂/Pic/25/1 | Ex 5 145° C. Temp | Ex 6 135° C. Temp | Ex 7 185° C. Temp | Ex 8 125° C. Temp |
|---|---|---|---|---|---|---|---|
| 2-Cl, 6-CCl₃ pyridine | 10.0% | 15.1% | 13.3% | 5.1% | 4.2% | 12.5% | 3.0% |
| 2,6-diCl, 3-CCl₃ pyridine (Cl, Cl, CCl₃) | 7.3% | 10.7% | 10.9% | 12.7% | 15.5% | 4.1% | 15.7% |
| 2,3,6-triCl, 4-CHCl₂ pyridine | 5.4% | — | — | 16.0% | 16.7% | — | 33.3% |
| 2,3,6-triCl, 4-CCl₃ pyridine | 8.1% | — | 2.9% | 11.8% | 15.6% | — | 22.8% |

An important variable in practice of the process of the present invention is the reaction temperature. In general, a 10° C.–15° C. temperature increase approximately doubles the rate of reaction, so there is a predictable relationship existing between reaction temperature and reaction residence time within the range of reaction temperature contemplated by the invention. In general, also, it has been determined that temperatures below about 135° C. are not practical from the point of view of realizing any substantial yield of the desired reaction products, and temperatures above 170° C. are also not practical from the same point of view in that other chlorinated reaction products are realized at higher temperatures.

The chlorination process described in U.S. Pat. No. 3,424,754 relies on chlorine gas sparging into the liquid reaction mass to dissolve the chlorine in the reaction mass and to mix the alpha-picoline hydrochloride with the initiator charge. According to Chemical Engineering Handbook, Perry, 3d Edition, page 1215 (1950), agitation produced by the degree of gas sparging involved in the process of U.S. Pat. No. 3,424,754 (estimated to be about 1.5 cubic foot per square foot minute at 200° C.) is usually too mild to move immiscible liquids with appreciable density differences into good contact with each other. In reactions as contemplated by the present invention, it is a practical necessity to maintain the reaction mass well mixed so that there is good contact and quick dispersion of the alpha-picoline hydrochloride into the diluent at the desired reaction temperatures (135° C. to 170° C.) because the polychlorinated alpha-picoline diluent and the alpha-picoline hydrochloride are immiscible and have substantially different densities (about 1.6 and about 1.2 grams per cubic centimeter, respectively), and because alpha-picoline hydrochloride is unstable in this temperature range, i.e. the salt tends to break down to its components, namely hydrogen chloride and alpha-picoline. If there is breakdown into the components, the hydrogen chloride is volatile and escapes through the vent system and alpha-picoline builds up in the lighter liquid phase.

It is taught in U.S. Pat. No. 3,424,754 that feeding alpha-picoline in any substantial quantity directly into a chlorination reaction at a temperature in excess of 140° C. results in intractable mixtures of tars and polymers. Such tendency to form higher molecular weight reaction products increases at higher reaction temperatures. Mixing and chlorine feed rates of the degree described in U.S. Pat. No. 3,424,754 tend to provide poor contact between the liquid phases of the reaction mass and allow the undesirable reaction of alpha-picoline hydrochloride as discussed above to proceed. In fact, based on the analytical data presented in the examples of U.S. Pat. No. 3,424,754, at least about 25% of the alpha-picoline hydrochloride is lost in such prior art process to formation of nonvolatiles.

It has been discovered that yields of volatile chlorinated picolines in excess of 99% and other new useful products are obtained when care is taken to ensure a high partial pressure of chlorine and sufficient mixing and quick dispersion of the alpha-picoline hydrochloride into a chlorine rich diluent which does not substantially compete for the available chlorine. This is accomplished by sparging chlorine (in excess of that needed for the reaction) and alpha-picoline hydrochloride near the bottom of the polychlorinated pyridine diluent charge. The mixing required to ensure adequate contact between the liquids and gas can be achieved by high gas flow rate sparging, mechanical agitation, or a combination of both. High gas flow rates as described by Braulich, A. J.; Ch. E. Journal, Volume 11, No. 1, pp 73–79, can achieve mixing a magnitude almost equivalent to high power input mechanical mixing. Several disadvantages are inherent in the use of high gas flow rates, however. They are:

(a) high entrainment of the reactor liquids to the quench column C1 where they are scrubbed with carbon tetrachloride and must be recycled to the reaction system.

(b) a large volume of chlorine gas which must be purified, dried, and recycled.

Another mode of operation to enhance mixing is to combine mechanical agitation with chlorine gas and alpha-picoline hydrochloride sparging to achieve the desired degree of mixing and excess chlorine. High maintenance of mechanical seals and agitators are some of the disadvantages of such a mechanical agitation system.

An increase in reactor back pressure aids in increasing the chlorine concentration in the diluent. The stoichiometric amount of chlorine reacted per pound of alpha-picoline fed is greater than 3 to 1 by weight. At least a 100% excess of stoichiometric chlorine required as feed is preferred to ensure that the alpha-picoline hydrochloride does not form undesirable tars and polymers. This feed rate ensures at least a 50% molar concentration of chlorine in the vapor above the reactors. Therefore, weight ratios of at least about 8:1 of chlorine to alpha-picoline being fed are deemed necessary in practice of the present process.

Several runs were tried where the gas and liquid spargers were just under the reaction mass liquid levels. This resulted in poor mixing, lower rates of reaction, and low yields of 3-chloro-2-trichloromethyl pyridine at a temperature of 155° C. Good agitation was achieved at the same chlorine gas and alpha-picoline hydrochloride flow rates per unit area, but with significantly higher liquid level depths above the sparger discharge streams. For example, at 155° C. and an 8:1 chlorine to alpha-picoline feed ratio and with a chlorine flow rate of 440 gms/hr but with the spargers just barely under liquid level resulted in about an 8% yield of 3-chloro-2-trichloromethyl pyridine while a similar run with better coverage of the sparger about a 20% yield of 3-chloro-2-trichloromethyl pyridine was obtained. In the lower yield example a 1 liter spherical reactor was used which had a diameter of about 4 inches and a liquid depth of about 1 inch over the sparger nozzle. In the higher yield example the liquid level over the sparger nozzle in a like reactor was about 3 inches. In both cases the sparger nozzles were separated by about 2 inches with the chlorine sparger nozzle pointed downwardly and the alpha-picoline hydrochloride sparger nozzle pointed at the chlorine sparger nozzle.

What is claimed is:

1. The process of non-catalytically chlorinating alpha-picoline hydrochloride in the liquid phase to produce at least a 14 percent by weight yield of 3-chloro-2-trichloromethyl pyridine based on alpha-picoline, said process comprising:
   (a) establishing in a reactor means a diluent reactor charge which is made up of chlorinated pyridine and/or chlorinated picoline compunds, and diluent being essentially nonreactive with chlorine under the reaction conditions to which the reactants in the reactor means are subjected;
   (b) while maintaining the reactor charge at a temperature of from about 135° C. to about 170° C., sparging chlorine and alpha-picoline hydrochloride into the reactor charge at the bottom thereof at a chlorine-to-picoline feed ratio of at least about 8:1 by weight in the absence of a catalyst and at a feed rate low enough so that any separation of the reactor charge into a second, lighter phase composed of unchlorinated alpha-picoline hydrochloride is less than about 10% of the reactor charge by volume, the excess of chlorine being fed to the reactor charge relative to the amount of alpha-picoline hydrochloride being fed thereto providing enhanced agitation of the reaction mass and sufficient chlorine to ensure that the chlorine partial pressure in the vapor space over the reactor charge is greater than 50%, and
   (c) continuing chlorine addition, and maintaining the reaction mass at a temperature within the range indicated, for a time sufficient to give a recoverable yield of at least 14 percent by weight of 3-chloro-2-trichloromethyl pyridine.

2. The process of claim 1, performed in a continuous batch mode and in a series of at least four reactors, with the first two reactors having initial, essentially inert diluent charges as in step (a) of claim 1, with the reaction conditions of step (b) of claim 1 being maintained in a first reactor, with excess chlorine, hydrogen chloride and entrained products being transferred by vent line and sparger from the first reactor to a second reactor, with overflow liquid products of chlorination being transferred from the first reactor to the second reactor, the volatile hydrochlorides being absorbed and reacted further in the second reactor, and with overflow liquid from the second reactor being transferred to a third reactor or alternatively to a fourth reactor into which third reactor or fourth reactor chlorine is sparged in a batch manner to further chlorinate substantially all reactive alpha-picoline hydrochloride present.

3. The process of claim 1, characterized by intermixing of the chlorine and alpha-picoline hydrochloride sparged to the reactor, such intermixing involving high gas flow rate sparging of the chlorine or mechanical agitation of the reaction mass, or a combination thereof.

4. The process of claim 3, involving a reaction temperature of about 155° C., and producing a reaction product wherein the yield of volatiles is at least about 98% and the yield of 3-chloro-2-trichloromethyl pyridine in relation to the alpha-picoline hydrochloride sparged to the reaction is at least about 20% by weight.

* * * * *